United States Patent [19]

Yamaguchi et al.

[11] Patent Number: 5,536,376

[45] Date of Patent: Jul. 16, 1996

[54] METHOD FOR PRODUCTION OF 2-CHLOROPYRIDINE AND 2,6-DICHLOROPYRIDINE

[75] Inventors: Shigenobu Yamaguchi; Johji Ogasahara; Hiroyuki Hata; Ryoichi Tokura; Hiromoto Shigeta, all of Hyogo, Japan

[73] Assignee: Sumitomo Seika Chemicals Co., Ltd., Hyogo, Japan

[21] Appl. No.: 174,018

[22] Filed: Dec. 28, 1993

[30] Foreign Application Priority Data

Dec. 28, 1992 [JP] Japan ............................ 4-360751
Feb. 25, 1993 [JP] Japan ............................ 5-063228
Jun. 21, 1993 [JP] Japan ............................ 5-174870

[51] Int. Cl.$^6$ .................................................. B01D 3/34
[52] U.S. Cl. ................................ 203/35; 203/95; 203/96; 203/DIG. 16; 204/157.71; 546/345
[58] Field of Search .................. 203/35, 92, 95, 203/96, DIG 16; 204/157.71, 157.48, 157.86, 158.2; 546/345, 286, 312

[56] References Cited

U.S. PATENT DOCUMENTS

| | | | |
|---|---|---|---|
| 3,297,556 | 1/1967 | Boudaklan et al. | 204/157.71 |
| 3,668,209 | 6/1972 | Kyriacou | 546/345 |
| 3,899,495 | 8/1975 | Beschke et al. | 546/345 |
| 3,969,205 | 7/1976 | Kawamura et al. | 204/157.71 |
| 4,054,499 | 10/1977 | Kawamura et al. | 204/157.71 |
| 5,141,608 | 8/1992 | Kamei | 204/157.71 |

FOREIGN PATENT DOCUMENTS

| | | | |
|---|---|---|---|
| 0708590 | 4/1965 | Canada | 204/157.71 |
| 0154266 | 12/1975 | Japan | 204/157.71 |
| 0154268 | 12/1975 | Japan | 204/157.71 |
| 55-004744 | 1/1980 | Japan . | |
| 55-004742 | 1/1980 | Japan . | |
| 1308256 | 12/1989 | Japan . | |
| 2268159 | 11/1990 | Japan . | |
| 3058971 | 3/1991 | Japan . | |

*Primary Examiner*—Virginia Manoharan
*Attorney, Agent, or Firm*—Birch, Stewart, Kolasch & Birch

[57] ABSTRACT

A method for producing 2-chloropyridine and 2,6-dichloropyridine by the steps of mixing vaporized chlorine and vaporized water to obtain dilute chlorine; introducing the dilute chlorine and vaporized pyridine into a reactor; and reacting the vaporized pyridine with the dilute chlorine in a gas phase under ultraviolet rays irradiation. By the method, 2-chloropyridine and 2,6-dichloropyridine can be produced in high yields. The present invention is also directed to a method for separating 2,6-dichloropyridine from a mixture containing 2,6-dichloropyridine, 2-chloropyridine and pyridine by the step of carrying out distillation of the mixture containing 2,6-dichloropyridine, 2-chloropyridine and pyridine in the presence of water while adding sulfuric acid to a distillation column. Highly purified 2,6-dichloropyridine can be separated by the method.

11 Claims, No Drawings

METHOD FOR PRODUCTION OF 2-CHLOROPYRIDINE AND 2,6-DICHLOROPYRIDINE

BACKGROUND OF THE INVENTION

1. Field of the Invention

The present invention relates to a method for producing 2-chloropyridine and 2,6-dichloropyridine by photochemically chlorinating pyridine in a gas phase. Also, the present invention relates to a method for efficiently separating 2,6-dichloropyridine from the aqueous reaction mixture containing 2,6-dichloropyridine, 2-chloropyridine and pyridine obtained by photochemical chlorination of pyridine using water as a diluent or thermal chlorination of pyridine. Both 2-chloropyridine and 2,6-dichloropyridine are important intermediates for medicines and agricultural chemicals.

2. Discussion of the Related Art

There are two methods known for obtaining 2-chloropyridine and 2,6-dichloropyridine by pyridine chlorination: thermal chlorination of pyridine at high temperatures of 370° to 430° C. (DE2208007) and photochemical chlorination of pyridine within the temperature range from about 78° to 125° C. under irradiation with a high pressure mercury lamp (U.S. Pat. No. 3,297,556).

Because the thermal chlorination method is carried out under high temperature conditions, condensation reactions of the resulting 2-chloropyridine and 2,6-dichloropyridine with the starting material pyridine occur to form tar, which in turn lowers the yield of the desired products. This method poses another problem, which is the difficulty of purification of the desired products from the reaction mixture due to the presence of a large amount of impurities in the reaction mixture. Also, since 2,6-dichloropyridine, one of the desired products, begins to decompose exothermally near 370° C. and decomposes rapidly at 380° C., as determined by differential thermal analysis, the thermal chlorination method is not preferable for obtaining 2,6-dichloropyridine.

On the other hand, the photochemical chlorination method is usually carried out in a gas phase by using a high pressure mercury lamp as a source of ultraviolet rays (UV), wherein pyridine, chlorine and a diluent, all in a vaporized state, are exposed to UV irradiation. Conventionally, there are two choices for the diluent, i.e., a halogenated hydrocarbon or water. When a halogenated hydrocarbon is used as the diluent, the above-mentioned problem of tar formation is unlikely to occur because the reaction temperature is usually 160° to 190° C., lower than that for the thermal chlorination method, and, therefore, a reaction mixture without impurities can be obtained. When water is used as the diluent, reaction temperature is also low, usually 160° to 170° C.

However, the heat of reaction in 2-chloropyridine production from pyridine is about 30 kcal/mol, and that in 2,6-dichloropyridine production from pyridine is about 60 kcal/mol; both reactions are highly exothermic. For this reason, compounds which do not undergo chlorination per se, such as carbon tetrachloride having a great molar specific heat, have been used as diluents for the reaction in order to remove such heat of reaction and maintain a low reaction temperature. However, the use of carbon tetrachloride is becoming difficult due to its carcinogenicity and the recent legal regulation on FLON (a chlorofluorocarbon product) and HALON (bromochlorofluorocarbons and bromochlorocarbons). Although other various halogenated hydrocarbons have been proposed as substitutes for carbon tetrachloride, none is free from the legal regulation on Flon and Halon and the problem of carcinogenicity. Accordingly, various methods using water as the diluent have recently been proposed.

Because the molar specific heat of water is much lower than that of gaseous carbon tetrachloride, removal of heat of reaction using steam requires more molar amount than that of carbon tetrachloride, as a diluent for the reaction. However, increasing the amount of diluent is disadvantageous because the reaction itself is decelerated due to dilution of pyridine and chlorine with the steam, though heat removing capability based on sensible heat increases. There is also a problem that removal of heat of reaction becomes difficult due to poor heat transfer through the reactor wall when the reaction is carried out in a gas phase. Thus, the conventional photochemical chlorination reaction is faulty in that experimental conditions cannot be applied directly to an increased scale of reaction. This is true not only when steam is used as a diluent, but also when carbon tetrachloride is used as a diluent. In other words, increasing the reactor size results in a decreased heat-transfer surface area per unit volume and hence a decreased total amount of heat removed through the reactor wall.

In the above situation, Japanese Patent Examined Publication Nos. 55-4742 and 52-3935 and Japanese Patent Laid-Open Nos. 1-207270 and 1-308256 propose methods using water as a diluent. In the preferred embodiments of these methods shown in the respective specifications, reactor capacity is 1 to 5 liter, remaining within the range of laboratory scale or intermediate experimental scale. On such scale, heat-transfer surface area per unit volume of the reactor is sufficient to remove heat of reaction, and photochemical chlorination is carried out usually at 160° to 170° C. as stated above by external cooling.

However, unlike laboratory-scale production, industrial production of 2-chloropyridine and 2,6-dichloropyridine requires a reactor capacity of at least 100 liters, usually 300 liters or more. On this scale, removal of the heat of reaction is very difficult because heat-transfer surface area per unit volume of the reactor decreases drastically.

Also, uniformly mixing three components, namely pyridine, chlorine and a diluent in a gas phase poses an important problem from the viewpoint of chemical reaction engineering. Specifically, localization of high concentration chlorine results in a local rise in reaction temperature, leading to an uneven distribution of high temperature portions in the reactor. Also, the resulting 2,6-dichloropyridine may undergo further chlorination by the action of the high concentration chlorine, which can increase amounts of by-products such as trichloropyridine and tetrachloropyridine.

As a solution to these problems, industrial production may be carried out using a number of small reactors, but such approach is unrealistic due to troublesome instrumentation and piping associated with the increased number of reactors.

Also, the amount of steam may be increased to remove heat of reaction and to dilute chlorine. In this method, however, excessive dilution lowers the chlorine and pyridine concentrations, resulting in decreased production per unit time. Moreover, this method is undesirable not only because isolation and purification of 2-chloropyridine and 2,6-dichloropyridine become difficult but also because increased discharge of waste water may become a problem in view of environmental protection.

Alternatively, reaction temperature itself may be set low to compensate for the occurrence of local hot portions due to uneven distribution of chlorine concentration, but this method is not industrially advantageous because of decreased productivity.

Concerning the separation of 2,6-dichloropyridine from the reaction mixture containing 2,6-dichloropyridine, 2-chloropyridine and pyridine obtained by photochemical chlorination or thermal chlorination of pyridine, various methods have been disclosed. Above all, the particularly efficient method is described in Japanese Patent Laid-Open No. 3-58971. This method separates and purifies 2,6-dichloropyridine from a reaction mixture of 2,6-dichloropyridine, 2-chloropyridine and pyridine by distillation in the presence of hydrogen chloride in a still.

However, in the method of Japanese Patent Laid-Open No. 3-58971, a high concentration of hydrogen chloride must be maintained during distillation to facilitate separation of 2,6-dichloropyridine by distillation. For maintaining such a high concentration of hydrogen chloride, a large amount of hydrochloric acid or sulfuric acid, depending on the composition of reaction mixture in the distillation still, must be added. In other words, the amount of hydrochloric acid added to the reaction mixture is determined by the degree of chlorination of pyridine. When it is desired to obtain 2,6-dichloropyridine in a larger amount than that of 2-chloropyridine by an increased degree of chlorination, the amount of hydrochloric acid formed increases, so that only a small amount of hydrochloric acid is required for distillation. However, when it is desired to obtain 2-chloropyridine in a larger amount than that of 2,6-dichloropyridine by a decreased degree of chlorination, a large amount of hydrochloric acid must be added because the amount of hydrochloric acid formed decreases. Also, for recovering 2-chloropyridine and pyridine from the reaction mixture after 2,6-dichloropyridine distillation, the reaction mixture must be adjusted to an appropriate pH level, which in turn requires the addition of alkali in an amount equivalent to the amount of acid added.

As stated above, the method of Japanese Patent Laid-Open No. 3-58971 is not satisfactory from economic viewpoint because a large amount of acid is required to be added at steam distillation, depending on the reaction mixture composition, and the acid must be neutralized in a series of recovery processes up to the recovery of 2-chloropyridine and unreacted pyridine, which in turn requires an increased amount of alkali.

Moreover, in the above method, a mixture of 2,6-dichloropyridine as an oil and water is obtained as a distillate, which contains hydrochloric acid and a small amount of 2-chloropyridine. Since this distillate can be separated into two layers, namely a water layer and an oil layer, and since the hydrochloric acid and 2-chloropyridine are mostly contained in the water layer, they are mostly removed along with water by liquid separation. However, a small amount of hydrochloric acid and 2-chloropyridine may be present in the oil layer containing 2,6-dichloropyridine, which can deteriorate the quality of 2,6-dichloropyridine. For this reason, the 2,6-dichloropyridine must be further treated by washing, etc. to obtain 2,6-dichloropyridine of high purity.

SUMMARY OF THE INVENTION

The above-mentioned problems concerning the production of 2-chloropyridine and 2,6-dichloropyridine did not occur in the prior arts wherein reactors of 1 to 5 liter capacity were used. Thus, on such small to medium scales as in the prior arts, photochemical chlorination can be carried out without special attention to removal of heat of reaction or uniform mixing of pyridine, chlorine and steam. Specifically, in the methods of prior arts, pyridine, chlorine and water are separately introduced into the reactor after vaporization via separate pipes, or they are previously mixed and then introduced into the reactor via a single pipe, or pyridine and water are mixed, vaporized and then introduced into the reactor, while chlorine is introduced via another pipe. No consideration is given to prevent the above-described localization of high concentration chlorine and, actually, uniformly mixing has been achieved without such consideration.

The present inventors investigated to apply the above-described prior art on an industrial scale. Consequently, the present inventors have found that the above problems are overcome to permit industrially advantageous photochemical chlorination of pyridine by introducing chlorine, previously diluted with steam, to the reactor and chlorinating the pyridine in a gas phase, and have thus completed the present invention.

The present inventors also investigated to develop a method for separating 2,6-dichloropyridine at high yield and high efficiency from the aqueous reaction mixture containing 2,6-dichloropyridine, 2-chloropyridine and pyridine obtained by photochemical chlorination of pyridine using water as a diluent or thermal chlorination of pyridine, particularly a method for saving the acid used for 2,6-dichloropyridine distillation in the presence of water. As a result, the present inventors have found that when sulfuric acid is added to a distillation column, rather than to a distillation still, the acid to be added can be saved, in comparison with the method of Japanese Patent Laid-Open No. 3-58971, and 2,6-dichloropyridine of higher purity is obtained because 2,6-dichloropyridine obtained by liquid separation from the distillate contains only trace amounts of hydrochloric acid and 2-chloropyridine. The inventors have made further investigations based on this finding, and developed the present invention.

Thus, the object of the present invention is to provide a method for efficiently producing 2-chloropyridine and 2,6-dichloropyridine on an industrial scale, wherein heat of reaction can efficiently be removed even on an industrial scale; pyridine, chlorine and steam can uniformly be mixed; and production of by-products can be minimized.

Another object of the present invention is to provide a method for efficiently separating 2,6-dichloropyridine from the aqueous reaction mixture containing dichloropyridine, 2-chloropyridine and pyridine obtained by photochemical chlorination using water as a diluent or thermal chlorination of pyridine, particularly such method as to reduce the amount of acid used during the distillation of 2,6-dichloropyridine in the presence of water.

Specifically, the present invention relates to a method for producing 2-chloropyridine and 2,6-dichloropyridine in which pyridine is reacted with chlorine in a gas phase using water as a diluent under UV irradiation. The method has the steps of mixing vaporized chlorine and vaporized water in advance and then introducing the resulting dilute chlorine into a reactor to chlorinate vaporized pyridine under ultraviolet irradiation. In the present invention, "dilute chlorine" means chlorine diluted with water obtained by mixing vaporized chlorine and vaporized water.

Also, the present invention relates to a method for separating 2,6-dichloropyridine from the aqueous reaction mixture containing 2,6-dichloropyridine, 2-chloropyridine and pyridine obtained by pyridine chlorination reaction. The method has the step of carrying out 2,6-dichloropyridine distillation in the presence of water while adding sulfuric acid to a distillation column.

According to the method of producing 2-chloropyridine and 2,6-dichloropyridine of the present invention, dilute chlorine obtained by previously mixing vaporized chlorine and vaporized water in a gas phase is introduced into a reactor, and vaporized pyridine is then uniformly mixed with the dilute chlorine in the reactor. Therefore, the reaction takes place uniformly in the entire reactor. Since temperature bias in the reactor decreases, it is unnecessary to set the reaction temperature low to compensate for the occurrence of hot portions due to local reaction. It can therefore be possible to set the reaction temperature higher than that in the prior art. Although there is a concern about increased production of highly chlorinated compounds such as trichloropyridine and tetrachloropyridine as by-products with rise of reaction temperature, the use of dilute chlorine in the present invention leads to selective chlorination reactions, thus producing 2-chloropyridine and 2,6-dichloropyridine at high yield and suppressing the production of highly chlorinated compounds.

According to the method of separating 2,6-dichloropyridine of the present invention, the following advantages over the conventional methods are obtained: the amount of acid added upon distillation can be kept small; 2,6-dichloropyridine of high purity can be obtained at a high recovery rate; and it can be operated by simple steps.

The advantages presented above are desirable for industrial application. Further, the method of the present invention is desirable also in view of environmental protection because it does not require the use of halogenated hydrocarbons, the substance of which carcinogenicity and ozonosphere destructive action are becoming a great environmental concern.

DETAILED DESCRIPTION OF THE INVENTION

In the method of producing 2-chloropyridine and 2,6-dichloropyridine of the present invention, the reaction is normally carried out at a reaction temperature of 180° C. to 300° C. Reaction temperatures of lower than 180° C. are undesirable because productivity lowers. Reaction temperatures exceeding 300° C. pose a problem of by-product formation. Evidently, this range of reaction temperature is considerably higher than the reaction temperature of 160° to 170° C. specified in all the Examples of the above-described prior art.

High reaction temperature settings are effective in removing more heat per unit time, because the sensible heat of the reaction gas in the reactor maintains large temperature differences between the reactor and the outside coolant. The inventors unexpectedly found that the amount of heat transferred to the outside coolant through the reactor wall increases as the reaction temperature rises. This is an unexpected finding, meaning that the value of overall coefficient of heat transfer (U), an index of thermal conductivity, increases as the reaction temperature rises.

For example, in the 520 liter reactor used in the Examples given below, the apparent overall coefficient of heat transfer U (kcal/m$^2$/hr/deg) increased in a geometric progression from 12.4 at 170° C. to 19.5 at 200° C., 30.1 at 230° C. and 42.0 at 260° C. Since the overall coefficient of heat transfer remains constant even when the flow rate of the gas in the reactor is changed, it depends solely on reaction temperature. Heat removal from the reactor wall is therefore facilitated with the rise in reaction temperature. This fact makes it possible to conduct photochemical chlorination at higher reaction temperatures, and, therefore, productivity can be expected to be improved.

To keep such a reaction temperature, a coolant temperature must also be considered. In the present invention, any coolant can be used, exemplified by steam, hot water and cooling oil, and preferable results can be obtained when the reaction is carried out while maintaining a coolant temperature of not lower than 70° C.

The amount of water used to dilute chlorine can be optionally chosen from the range of 1 to 30 times the amount of chlorine, as of the volume of steam in vaporized state. In other words, if the volume of steam is less than 1 time the volume of chlorine, the chlorine gas fails to have a diluting effect. If the volume of steam exceeds 30 times the volume of chlorine, productivity decreases, and the post-treatment becomes undesirably troublesome.

Steam can be used to dilute pyridine as well as chlorine. In other words, depending on reaction conditions, good results may be obtained when pyridine as well as chlorine is used in the form of a diluted mixture with water in a gas phase (i.e. dilute pyridine). In the present invention, "dilute pyridine" means pyridine diluted with water obtained by mixing vaporized pyridine and vaporized water.

From the viewpoint of volume efficiency, the total amount of steam used to dilute both chlorine and pyridine as described above is appropriately in the range from 10 to 30 mol per mol of pyridine.

Reagents are introduced into the reactor via two kinds of pipes, namely pyridine introduction pipes (vaporized pyridine or dilute pyridine) and chlorine introduction pipes (dilute chlorine). Although a single pipe is acceptable for each kind of reagent introduction pipe, the reaction can be more uniformly carried out when two or more pipes of each kind are used. Here, the molar ratio of the reagents (pyridine, chlorine and water) introduced into the reactor is normally 1:0.3–10:10:30.

The reaction proceeds smoothly as a result of uniform mixing in the reactor when the gas is sparged tangentially to the reactor wall.

After completion of the reaction, the reaction gas is exhausted from the lower part of the reactor, cooled to condense and then subjected to the separation/purification process of 2-chloropyridine and 2,6-dichloropyridine. From the obtained mixture containing 2-chloropyridine, 2,6-dichloropyridine and pyridine, 2,6-dichloropyridine can efficiently be separated by the method of the present invention as described below.

In the separating method of the present invention, 2,6-dichloropyridine is obtained at high purity by distillation in the presence of water with addition of sulfuric acid to a distillation column. This is probably because 2,6-dichloropyridine does not form a salt with sulfuric acid and is hence distilled off in the form of vapor. By contrast, 2-chloropyridine and pyridine remain undistilled due to decreased vapor pressures since they react with sulfuric acid to form respective salts and lower their vapor pressures, when distillation is conducted in the presence of sulfuric acid and water. In comparison with the method described in Japanese Patent Laid-Open No. 3-58971, the present method is featured as follows:

1) Added sulfuric acid is easier to form a salt with 2-chloropyridine than hydrochloric acid.
2) Contact efficiency and salt-forming efficiency of 2-chloropyridine and pyridine with sulfuric acid can be improved by adding sulfuric acid to the distillation column rather than to the distillation still.

3) Unlike hydrochloric acid, sulfuric acid is non-volatile and hence it is not distilled out from the top of the distillation column. With these features, the present method offers highly purified 2,6-dichloropyridine containing smaller amounts of hydrochloric acid, 2-chloropyridine and pyridine, allowing separation of 2,6-dichloropyridine from the reaction mixture at high yield and high efficiency.

The mixture to be treated by the method of the present invention is a mixture containing 2,6-dichloropyridine, 2-chloropyridine and pyridine, exemplified by the aqueous reaction mixture obtained by photochemical chlorination of pyridine using water as a diluent or thermal chlorination of pyridine. Here, the photochemical chlorination of pyridine can be carried out by the present invention or any method described in prior arts. Among them, it is preferred to use the reaction mixture obtained by the photochemical chlorination of pyridine according to the present invention described above. The composition of mixture used in the method of the present invention is not particularly limitative.

Any ordinary distiller can be used for the method of the present invention. For example, distillation stills and distillation columns of various types such as the plate column type and the packed column type can be used in combination. The plate column type distillation column may have a bubble cap tray, a sieve tray, a valve-type tray or the like. The packed type column may have a random packing such as a Raschig ring, a Lessing ring and a pall ring, or an ordered arrangement packing such as Technopac™ (manufactured by Kawasaki Engineering Japan).

The above-described reaction mixture for the present invention may be placed in the distillation still before distillation, or when sulfuric acid is continuously added to the distillation column, the reaction mixture may be continuously added to the distillation column at the same level as, or lower than, the site of sulfuric acid addition. It is also effective to previously mix sulfuric acid with the reaction mixture and then add the mixture to the distillation column. The amount of sulfuric acid as pure $H_2SO_4$ added to the distillation column is normally 0.02 to 0.3 by weight of the reaction mixture.

Any method can be employed to add sulfuric acid to the distillation column without limitation, as long as the sulfuric acid is allowed to contact with gaseous mixture in the distillation column, exemplified by continuous or intermittent addition of sulfuric acid. In this case, sulfuric acid may be added to any site without limitation, as long as the sulfuric acid added is allowed to satisfactorily contact with the 2-chloropyridine, 2,6-dichloropyridine and pyridine rising in the distillation column with the progress of distillation. However, the site of addition is preferably located between the central portion and top of the distillation column, because 2,6-dichloropyridine can be much more efficiently separated in such cases. Timing of addition of sulfuric acid is also subject to no limitation, and it is adjusted according to distillation conditions.

Also, when sulfuric acid is continuously added to the distillation column as stated above, 2,6-dichloropyridine is continuously obtained in the distillate, provided that distillation is conducted in the presence of water while continuously adding a mixture, e.g. a reaction mixture obtained by photochemical chlorination of pyridine using water as a diluent, to the distillation column at the same level as, or lower than, the site of addition of sulfuric acid. The reaction mixture is added, for example, at a position between 0 and 150 mm from the top of a distillation column having a height of 300 mm. Since pyridine and 2-chloropyridine form respective salts with sulfuric acid and flow down in the distillation column along with hydrochloric acid and sulfuric acid, 2,6-dichloropyridine can be separated from the top of the column by a continuous process. In this case, although the site of sulfuric acid addition is not subject to limitation, it is preferably located between the central portion and top of the distillation column as described above. This method also allows significant reduction in the amount of sulfuric acid used, since contact efficiency between the pyridine or 2-chloropyridine in the mixture and sulfuric acid improves. The liquid containing pyridine salts and 2-chloropyridine salts can be continuously taken out from the distillation still, followed by pyridine salts and 2-chloropyridine isolation by a known method such as the method described in Japanese Patent Laid-Open No. 3-58971.

The efficiency of fractional distillation of 2,6-dichloropyridine increases as the sulfuric acid concentration increases; the sulfuric acid concentration is normally required to be not lower than 5 wt %, preferably not lower than 10 wt % as of an aqueous solution. Sulfuric acid concentrations of lower than 5 wt % are undesirable, though 2,6-dichloropyridine separation proceeds satisfactorily, because the amount of sulfuric acid added increases, which in turn increases the liquid volume in the distillation column and hence decreases the treated amount per unit time.

The amount of sulfuric acid added to the distillation column may be adjusted according to the composition of the mixture to be distilled (e.g., reaction mixture), and is generally required to be sufficient to react with the 2-chloropyridine and pyridine rising in the distillation column with the progress of distillation in the presence of water to form respective salts. Specifically, the amount of sulfuric acid as pure $H_2SO_4$ added to the distillation column is normally 0.02 to 0.3 by weight of the reaction mixture.

In the present invention, 2,6-dichloropyridine of high purity can be obtained in the 2,6-dichloropyridine-water distillate from the distillation column solely by filtration, since the 2,6-dichloropyridine separates as a solid upon cooling. Alternatively, highly purified 2,6-dichloropyridine can be obtained by liquid separation from the distillate under heating conditions at not lower than 90° C., because the melting point of 2,6-dichloropyridine is 87° C. In this case, since the filtrate resulting from 2,6-dichloropyridine filtration or the water layer obtained by liquid separation contains a small amount of 2,6-dichloropyridine dissolved therein, 2,6-dichloropyridine yield can be improved by recycling the filtrate or water layer in the distillation column after addition of sulfuric acid.

Highly purified 2,6-dichloropyridine can be thus separated from the reaction mixture obtained by reacting pyridine with chlorine in the presence of water as a diluent and then by distilling the reaction mixture in the presence of water and sulfuric acid without organic solvent extraction.

EXAMPLE

The present invention is hereinafter described in more details by means of the following working examples, but the present invention is not limited by them.

Example 1

Using a 520 liter glass-lined reactor, equipped with a high pressure mercury lamp, pyridine was subjected to a photochemical chlorination reaction at a reaction temperature of 194° C. Two pyridine-sparging pipes and two chlorine-sparging pipes were attached to the reactor wall in alternatively symmetrical positions. The gases were sparged tangentially to the reactor wall.

The reaction was carried out in a 1:1.58:18.9 molar ratio of pyridine, chlorine and water, in which pyridine was introduced at a rate of 16.0 kg/hr via the pyridine-sparging pipes, while 22.7 kg/hr chlorine and 68.9 kg/hr water were vaporized, mixed and diluted and then introduced via the chlorine-sparging pipes.

When the reaction was carried out under the above conditions with a reaction gas residence time of 19.2 seconds, 19.4 g per liter of reactor volume per hour (hereinafter referred to as g/liter/hr) of 2-chloropyridine and 27.9 g/liter/hr of 2,6-dichloropyridine were produced. There obtained 10.1 kg/hr of 2-chloropyridine and 14.5 kg/hr of 2,6-dichloropyridine. The yield based on pyridine (hereinafter referred to simply as yield) was 43.9% and 48.3%, respectively. The pyridine chlorination rate was 92.5%, and the yield of trichloropyridine, a by-product, was 0.3%.

Example 2

A photochemical chlorination was carried out in the same way as in Example 1 except for employing a 1:1.39:16.2 molar ratio of pyridine, chlorine and water and a reaction temperature of 200° C.

27.4 kg/hr of chlorine was mixed and diluted with 27.8 kg/hr of water vapor, and introduced via the chlorine-sparging pipes. Similarly, 53.1 kg/hr of water was vaporized, mixed with 21.9 kg/hr of pyridine, and introduced into the reactor via the pyridine-sparging pipes.

When the reaction was carried out under the above conditions with a reaction gas residence time of 16.2 seconds, 34.4 g/liter/hr of 2-chloropyridine, 25.8 g/liter/hr of 2,6-dichloropyridine were produced. There obtained 17.9 kg/hr (yield 56.8%) of 2-chloropyridine and 13.4 kg/hr (yield 32.7%) of 2,6-dichloropyridine. The chlorination rate of pyridine was 89.7%, and the yield of trichloropyridine was 0.2%.

Example 3

A photochemical chlorination was carried out in the same way as in Example 1 except for employing a 1:0.73:13.8 molar ratio of pyridine, chlorine and water; and a reaction temperature of 184° C.

19.9 kg/hr of chlorine was mixed and diluted with 95.5 kg/hr of water vapor, and introduced via the chlorine-sparging pipes, while 30.4 kg/hr of pyridine was introduced into the reactor via the pyridine-sparging pipes.

When the reaction was carried out under the above conditions with a reaction gas residence time of 14.0 seconds, 45.0 g/liter/hr of 2-chloropyridine, 7.4 g/liter/hr of 2,6-dichloropyridine were produced, i.e., 23.4 kg/hr (yield 53.6%) of 2-chloropyridine and 3.9 kg/hr (yield 6.8%) of 2,6-dichloropyridine were obtained. The pyridine chlorination rate was 60.4%, and production of trichloropyridine did not occur.

Example 4

A photochemical chlorination was carried out using a reactor with a capacity of 1000 liters having three pyridine-sparging pipes and three chlorine-sparging pipes.

The same conditions as in Example 2 except for employing a reaction temperature of 230° C.

When the reaction was carried out under the above conditions with a reaction gas residence time of 11.5 seconds, 46.1 g/liter/hr of 2-chloropyridine, 35.8 g/liter/hr of 2,6-dichloropyridine were produced, i.e., 46.1 kg/hr (yield 56.3%) of 2-chloropyridine and 35.8 kg/hr (yield 33.5%) of 2,6-dichloropyridine were obtained. The chlorination rate of pyridine was 90.0%, and the yield of trichloropyridine was 0.2%.

Example 5

Using water as a diluent, pyridine was subjected to a photochemical chlorination reaction to yield a reaction mixture containing 15.2 g of pyridine, 78.0 g of 2-chloropyridine, 146.0 g of 2,6-dichloropyridine, 96.6 g of hydrogen sulfide and 441.8 g of water.

This reaction mixture was placed in a 2 liter four-necked flask (distillation still) equipped with a 30 mm dia.×300 mm packed height column packed with a ceramic Raschig ring (4 mm dia.×2 mm dia.×4 mm) and distilled, while adding 25 g of 70% sulfuric acid to the top of the packed column and 500 g of water to the distillation still over a period of 60 minutes. 714.3 g of the resulting distillate contained 145.1 g (recovery rate 99.4%) of 2,6-dichloropyridine and 1.5 g of hydrogen chloride, but not sulfuric acid.

This distillate was subjected to liquid-liquid separation while keeping hot (95° C.) to separate 2,6-dichloropyridine. The resulting 2,6-dichloropyridine was found to have a purity of 99.8% as determined by gas chromatography and contain neither 2-chloropyridine nor pyridine. The hydrogen chloride content was 0.03 wt %.

Example 6

The separation of 2,6-dichloropyridine was conducted in the same way as in Example 5 except that 70% sulfuric acid was added at a position 150 mm below the top of the distillation column. 705.7 g of the resulting distillate contained 145.6 g (recovery rate 99.7%) of 2,6-dichloropyridine and 3.1 g of hydrogen chloride but not contained sulfuric acid.

This distillate was subjected to liquid-liquid separation while keeping hot (95° C.) to separate 2,6-dichloropyridine. The resulting 2,6-dichloropyridine was found to have a purity of 99.8% as determined by gas chromatography and contain neither 2-chloropyridine nor pyridine. The hydrogen chloride content was 0.06%.

Example 7

Using water as a diluent, pyridine was subjected to a photochemical chlorination reaction to yield a reaction mixture containing 36.9 g of pyridine, 114.3 g of 2-chloropyridine, 57.8 g of 2,6-dichloropyridine, 65.3 g of hydrogen sulfide and 626.6 g of water.

This reaction mixture was placed in a 2 liter four-necked flask (distillation still) equipped with a 30 mm dia.×300 mm packed height column packed with a ceramic Raschig ring (4 mm dia.×2 mm dia.×4 mm) and distilled, while adding 50 g of 70% sulfuric acid from the top of the packed column and 200 g of water to the distillation still over a period of 30 minutes. 283.5 g of the resulting distillate contained 57.7 g (recovery rate 99.8%) of 2,6-dichloropyridine and 0.2 g of hydrogen chloride, but not contained sulfuric acid:

This distillate was subjected to liquid-liquid separation while keeping hot (95° C.) to separate 2,6-dichloropyridine. The resulting 2,6-dichloropyridine was found to have a purity of 99.8% as determined by gas chromatography and not to contain 2-chloropyridine, pyridine and hydrogen chloride.

Example 8

While the same reaction mixture as that used in Example 7 was continuously added to the distillation column at the position 150 mm below the top of the column and distilled, 70% sulfuric acid was continuously added from the top of the column. The mixture solution containing salts of 2-chloropyridine and pyridine was continuously taken out from the distillation still. 290.9 g of the distillate obtained from the top of the distillation column contained 57.6 g (recovery rate 99.7%) of 2,6-dichloropyridine and 0.6 g of hydrogen chloride but not contained sulfuric acid.

This distillate was subjected to liquid-liquid separation while keeping hot (95° C.) to separate 2,6-dichloropyridine. The resulting 2,6-dichloropyridine was found to have a purity of 99.8% as determined by gas chromatography and contain neither 2-chloropyridine nor pyridine. The content of hydrogen chloride was 0.1%.

Example 9

While the same reaction mixture as that used in Example 7, which was previously mixed with 100 g of 70% sulfuric acid, was continuously added to the distillation column at the position 150 mm below the top of the column and distilled. The mixture solution containing salts of 2-chloropyridine and pyridine was continuously taken out from the distillation still. 285.0 g of the distillate obtained from the top of the distillation column contained 57.7 g (recovery rate 99.8%) of 2,6-dichloropyridine and 0.3 g of hydrogen chloride, but not contained sulfuric acid.

This distillate was subjected to liquid-liquid separation while keeping hot (95° C.) to separate 2,6-dichloropyridine. The resulting 2,6-dichloropyridine was found to have a purity of 99.9% as determined by gas chromatography and contain neither 2-chloropyridine nor pyridine. The content of hydrogen chloride was 0.1%.

Comparative Example 1

In a setting otherwise comparable to Example 1, chlorine was introduced into the reactor without being diluted, while the total amount of vaporized water was mixed with pyridine and introduced into the reactor via the pyridine-sparging pipes. The molar ratio of pyridine, chlorine and water was the same as that in Example 1, but the rate of pyridine was 8.3 kg/hr. When a photochemical chlorination was carried out at a reaction temperature of 170° C. and with reaction gas residence time of 43.0 seconds, 10.5 g/liter/hr of 2-chloropyridine and 11.2 g/liter/hr of 2,6-dichloropyridine were produced. There obtained 5.5 kg/hr (yield 46.0%) of 2-chloropyridine and 5.8 kg/hr (yield 37.5%) of 2,6-dichloropyridine. The pyridine chlorination rate was 85.1%, and the yield of trichloropyridine was 1.6%.

Comparative Example 2

A photochemical chlorination was carried out under the same conditions as those in Comparative Example 1 except for employing a 1:0.70:14.4 molar ratio of pyridine, chlorine and water and a reaction gas residence time of 23.0 seconds.

As a result, 19.5 g/liter/hr of 2-chloropyridine and 8.4 g/liter/hr of 2,6-dichloropyridine were produced. 10.1 kg/hr (yield 39.5%) of 2-chloropyridine and 4.3 kg/hr (yield 13.0%) of 2,6-dichloropyridine were obtained. The pyridine chlorination rate was 52.9%, and the yield of trichloropyridine was 0.4%.

Comparative Example 3

The same reaction mixture as used in Example 7 was placed in a 2 liter four-necked flask (distillation still) equipped with a 30 mm dia.×300 mm packed height column packed with a ceramic Raschig ring (4 mm dia.×2 mm dia. ×4 mm) and distilled, while adding 180 g of 70% sulfuric acid and 200 g of water to the distillation still. 291.5 g of the resulting distillate contained 57.2 g (recovery rate 99.0%) of 2,6-dichloropyridine, 0.7 g of 2-chloropyridine and 7.8 g of hydrogen chloride, but contained neither sulfuric acid nor pyridine.

This distillate was subjected to liquid-liquid separation while keeping hot (95° C.) to separate 2,6-dichloropyridine. The resulting 2,6-dichloropyridine was found to have a purity of 99.2% as determined by gas chromatography and contain 0.2 g of 2-chloropyridine and 0.7 g of hydrogen chloride.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing 2,6-dichloropyridine, which comprises the steps of mixing vaporized chlorine and vaporized water to obtain dilute chlorine; introducing the dilute chlorine and vaporized pyridine or vaporized dilute pyridine into a reactor; reacting the vaporized pyridine or vaporized dilute pyridine with the dilute chlorine in a gas phase under ultraviolet ray irradiation to obtain a mixture containing 2,6-dichloropyridine, 2-chloropyridine and pyridine; carrying out distillation of the mixture containing 2,6-dichloropyridine, 2-chloropyridine and pyridine in the presence of water and sulfuric acid, wherein said sulfuric acid is added to a distillation column; and separating 2,6-dichloropyridine as product.

2. The method according to claim 1, wherein the amount of water used to dilute chlorine is a volume of 1 to 30 times that of chlorine in vaporized state.

3. The method according to claim 1, wherein the reaction is carried out at the temperature range of 180° to 300° C.

4. The method according to claim 1, wherein said vaporized dilute pyridine is obtained by mixing vaporized pyridine with vaporized water.

5. The method for claim 4, wherein the amount of water used to dilute both chlorine and pyridine is in the range from 10 to 30 mol per mol of pyridine.

6. The method according to claim 1, wherein the distillation is carried out in the presence of water by continuously adding said sulfuric acid to the distillation column, and wherein the mixture is continuously added to the distillation column at the same level as, or lower than the level of said sulfuric acid addition.

7. The method according to claim 1, wherein said sulfuric acid previously mixed with the mixture is added to the distillation column.

8. The method according to claim 1, wherein said sulfuric acid is added to a position between a central portion and top of the distillation column.

9. The method according to claim 1, wherein the sulfuric acid added has a concentration of not lower than 5 wt %.

10. The method according to claim 1, wherein the amount of sulfuric acid as pure $H_2SO_4$ added to the distillation column is normally 0.02 to 0.3 by weight of the reaction mixture.

11. The method according to claim 1, wherein a molar ratio of pyridine, chlorine and vaporized water reacted under ultraviolet ray irradiation is 1:0.3–10: 10–30, respectively.

* * * * *